United States Patent [19]

Shaber et al.

[11] Patent Number: 4,895,865
[45] Date of Patent: Jan. 23, 1990

[54] ALPHA-(2-ALKOXYPHENYL)-ALPHA-ALKYL-1H-1,2,4-TRIAZOLE-1-PROPANENITRILES AND DERIVATIVES

[75] Inventors: Steven H. Shaber, Horsham; Ted T. Fujimoto, Churchville, both of Pa.

[73] Assignee: Rohm and Haas Company, Philadelphia, Pa.

[21] Appl. No.: 936,782

[22] Filed: Dec. 9, 1986

Related U.S. Application Data

[63] Continuation-in-part of Ser. No. 817,636, Jan. 10, 1986, abandoned.

[51] Int. Cl.$^4$ ................. A01N 43/653; C07D 249/08
[52] U.S. Cl. .................... 514/383; 514/184; 548/101; 548/262
[58] Field of Search ............... 548/101, 262; 514/184, 514/383

[56] References Cited

U.S. PATENT DOCUMENTS

| | | | |
|---|---|---|---|
| 4,366,165 | 12/1982 | Miller et al. | 548/262 |
| 4,507,140 | 3/1985 | Sugaranam | 548/262 |
| 4,715,887 | 12/1987 | Kramer et al. | 548/262 |

FOREIGN PATENT DOCUMENTS

| | | | |
|---|---|---|---|
| 061840 | 6/1982 | European Pat. Off. | 548/262 |
| 145294 | 6/1985 | European Pat. Off. | 548/262 |

OTHER PUBLICATIONS

Mitsudera et al., "Synthesis and Fungicidal, etc." J. Takeda Res. Lev. 41 (1982) pp. 148–153.

Primary Examiner—Richard L. Raymond
Assistant Examiner—Patricia L. Morris
Attorney, Agent, or Firm—Polly E. Ramstad

[57] ABSTRACT

This invention relates to alpha-(2-alkoxyphenyl)-alpha-alkyl-1H-1,2,4-triazole-1-propanenitriles and derivatives, their enantiomorphs, acid addition salts and metal salt complexes. These compounds, enantiomorphs, salts and complexes are highly active broad-spectrum systemic fungicides effective in controlling phytopathogenic fungi such as barley helminthosporium, cucumber downy mildew, cucumber powdery mildew, grape downy mildew, peanut cercospora, rice blast, wheat powdery mildew and wheat stem rust. The compounds have protective and curative activity against rice blast when they are applied foliarly or systemically and have superior residual activity against rice blast via foliar application.

31 Claims, No Drawings

ALPHA-(2-ALKOXYPHENYL)-ALPHA-ALKYL-1H-1,2,4-TRIAZOLE-1-PROPANENITRILES AND DERIVATIVES

BACKGROUND OF THE INVENTION

This application is a continuation-in-part of pending application Ser. No. 817,636, filed Jan. 10, 1986, now abandoned.

This invention relates to alpha-(2-alkoxyphenyl)-alpha-alkyl-1H-1,2,4-triazole-1-propanenitriles and their use in controlling phytopathogenic fungi.

U.S. Pat. No. 4,366,165 discloses 1- and 4-arylcyanoalkyl-1,2,4-triazoles and their use against phytopathogenic fungi. However, it fails to recognize the particular class of compounds of the present invention which have a particularly high degree of fungicidal activity. While the term "aryl" was defined in '165 to include ($C_1$–$C_4$)alkoxy substituted phenyl, none of the examples which were made or the typical examples listed in '165 include members of the present class of compounds.

Mitsudera et al., J. Takeda Res. Lev., 41(3/4), 148-153, published December 1982, (related Japanese Pat. No. J59104367-A) discloses alpha-i-propyl-alpha-[(1,2,4-triazol-1-yl)methyl]-alpha-(4-methoxyphenyl)acetonitrile. This compound, while an alkoxy substituted phenyl acetonitrile compound, it is not a member of the present class of compounds. Further, Mitsudera et al. teach away from the present invention. They teach a preference for the halogen substituted phenyl, lower alkyl substituted cyanoalkyl triazole over the alkoxy substituted phenyl, lower alkyl substituted cyanoalkyl triazole.

It is totally unexpected and unobvious that the 2-alkoxyphenyl compounds of the present invention yield superior fungicidal activity when compared to the 4-alkoxyphenyls. Further, it is unobvious that the 2-alkoxyphenyl substituted propanenitriles would be superior to the 2-halophenyl substituted propanenitriles in view of Mitsudera et al.

DESCRIPTION OF THE INVENTION

In accordance with the present invention, there is provided a new class of triazole propanenitriles which are alpha-(2-alkoxvphenyl)-alpha-alkyl-1H-1,2,4-triazole-1-propanenitriles of the formula (I):

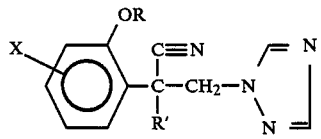

wherein R is hydrogen, ($C_1$–$C_6$)alkyl or ($C_2$–$C_5$)alkenyl; R' is optionally halogen substituted ($C_1$–$C_8$)alkyl, optionally halogen substituted ($C_2$–$C_6$)alkenyl, ($C_3$–$C_6$)cycloalkyl or ($C_1$–$C_3$)alkyl($C_3$–$C_6$)cycloalkyl; X is hydrogen or halogen; and the agronomically acceptable enantiomorphs, acid addition salts and metal complexes thereof.

The term "alkyl" is meant to include both branched and straight chained alkyl groups of carbon atoms. Typical alkyl groups which are encompassed by the use of this term include methyl, ethyl, n-propyl, iso-propyl, n-butyl, sec-butyl, iso-butyl, tert-butyl, pentyl, neopentyl, iso-pentyl, hexyl, heptyl, iso-octyl and the like.

The term "alkoxy," as used in the present specification, is meant to include hydroxy and alkenoxy, as well as the radical consisting of an alkyl group bonded to an oxygen atom. The preferred groups include hydroxy and ($C_1$–$C_6$)alkoxy. Typical alkoxy groups which are encompassed by the use of the term include hydroxy, methoxy, ethoxy, propoxy, n-butoxy, iso-butoxy, pentoxy, hexoxy and allyloxy.

Straight chain alkyl groups are preferred for both the R and R'. If the alkyl group for R' is branched, it is preferred that the branching does not occur at the alpha carbon of the R' substituent.

The acids which can be utilized in making the acid addition salts of the present invention include, for example, hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric and phthalic acids.

Another embodiment of this invention is the metal salt complexes of the formula (II):

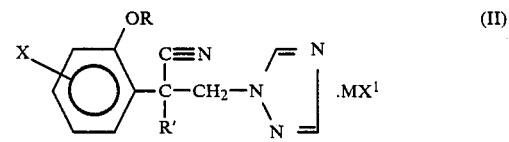

wherein R, R' and X are as defined in formula (I) above and M is a cation selected from Group IIA, IB, IIB, VIB, VIIB and VIII of the Periodic Table and $X^1$ is an anion selected so that the sum of the valence charges of the cation M and anion $X^1$ equal zero.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartrate, malate, maleate, fumarate, D-toluenesulfonate, methanesulfonate, mono- or di-($C_1$–$C_4$)alkyldithiocarbamate, ($C_1$–$C_4$)alkylenebisdithiocarbamate and the like.

A preferred embodiment of this invention is the compounds, agronomically acceptable enantiomorphs, salts and complexes of formulas (I) and (II) wherein X is hydrogen, R is hydrogen or ($C_1$–$C_6$)alkyl and R' is ($C_1$–$C_8$)alkyl. A more preferred embodiment of this invention is where X is a hydrogen, R is ($C_1$–$C_3$)alkyl and R' is ($C_3$–$C_5$)alkyl. A most preferred embodiment is where X is 5-halogen, R is methyl or ethyl and R' is n-butyl or n-propyl.

Typical compounds encompassed by the present invention include the following samples:

1. alpha-(2-methoxyphenyl)-alpha-methyl-b 1H-1,2,4-triazole-1-propanenitrile
2. alpha-(2-methoxyphenyl)-alpha-n-propyl-1H-1,2,4-triazole-1-propanenitrile
3. alpha-n-butyl-alpha-(2-methoxyphenyl)-1H-1,2,4-triazole-1-propanenitrile
4. alpha-iso-butyl-alpha-(2-methoxyphenyl)-1H-1,2,4-triazole-1-propanenitrile
5. alpha-(2-methoxyphenyl)-aloha-n-pentyl-1H-1,2,4-triazole-1-propanenitrile
6. alpha-(2-methoxyphenyl)-alpha-iso-pentyl-1H-1,2,4-triazole-1-propanenitrile 7. alpha-n-hexyl-alpha-(2-methoxyphenyl)-1H-1,2,4-triazole-1-propanenitrile
8. alpha-(2-ethoxyphenyl)-alpha-n-propyl-1H-1,2,4-triazole-1-propanenitrile
9. alpha-n-butyl-alpha-(2-ethoxyphenyl)-1H-1,2,4-triazole-1-propanenitrile
10. alpha-iso-butyl-alpha-(2-ethoxyphenyl)-1H-1,2,4-triazole-1-propanenitrile
11. alpha-(2-ethoxyphenyl)-alpha-n-pentyl-1H-1,2,4-triazole-1-propanenitrile
12. alpha-(2-ethoxyphenyl)-alpha-iso-pentyl-1H-1,2,4-triazole-1-propanenitrile
13. alpha-(2-propoxyphenyl)-alpha-n-propyl-1H-1,2,4-triazole-1-propanenitrile
14. alpha-n-butyl-alpha-(2-propoxyphenyl)-1H-1,2,4-triazole-1-propanenitrile
15. alpha-iso-butyl-alpha-(2-propoxyphenyl)-1H-1,2,4-triazole-1-propanenitrile
16. alpha-n-pentyl-alpha-(2-propoxyphenyl)-1H-1,2,4-triazole-1-propanenitrile
17. alpha-(2-butoxyphenyl)-alpha-n-butyl-1H-1,2,4-triazole-1-propanenitrile
18. alpha-n-butyl-alpha-(2-pentoxyphenyl)-1H-1,2,4-triazole-1-propanenitrile
19. alpha-n-butyl-alpha-(2-methoxy-4-chlorophenyl)-1H-1,2,4-triazole-1-propanenitrile
20. aloha-n-butyl-alpha-(2-iso-propoxyphenyl)-1H-1,2,4-triazole-1-propanenitrile
21. alpha-(2-allyloxyphenyl)-alpha-n-butyl-1H-1,2,4-triazole-1-propanenitrile
22. alpha-n-butyl-alpha-(5-chloro-2-methoxyphenyl)-1H-1,2,4-triazole-1-propanenitrile.
23. aloha-(5-chloro-2-methoxyphenyl)-alpha-n-propyl-1H-1,2,4-triazole-1-propanenitrile.
24. alpha-n-butyl-alpha-(5-chloro-2-ethoxyphenyl)-1H-1,2,4-triazole-1-propanenitrile.
25. alpha-(5-chloro-2-ethoxyphenyl)-alpha-n-propyl-1H-1,2,4-triazole-1-propanenitrile.
26. alpha-2-methoxyphenyl-alpha-4,4,4-trifluorobutyl-1H-1,2,4-triazole-1propanenitrile.
27. alpha-3-butenyl-alpha-2-methoxyphenyl-1H-1,2,4-triazole-1-propanenitrile.
28. alpha-2-ethoxyphenyl-alpha-4,,4-trifluorobutyl-1H-1,2,4-triazole-1-propanenitrile.
29. alpha-2-butenyl-alpha-2-ethoxyphenyl-1H-1,2,4-triazole-1-propanenitrile.
30. alpha-2-methoxyphenyl-alpha-2-propenyl-1H-1,2,4-triazole-1-propanenitrile.
31. alpha-(2-chloro-2-propenyl)-alpha-2-methoxyphenyl-1H-1,2,4-triazole-1propanenitrile.
32. alpha-cyclopropylmethyl-alpha-2-methoxyphenyl-1H-1,2,4-triazole-1-propanenitrile.

Comparative samples which were made include:
C1   alpha-n-butyl-alpha-phenyl-1H-1,2,4-triazole-1propanenitrile
C2.   alpha-phenyl-alpha-n-propyl-1H-1,2,4-triazole-1propanenitrile
C3.   alpha-n-pentyl-alpha-phenyl-1H-1,2,4-triazole-1propanenitrile
C4.   alpha-n-butyl-alpha-(2-fluorophenyl)-1H-1,2,4-triazole-1-propanenitrile
C5.   alpha-n-butyl-alpha-(2-chlorophenyl)-1H-1,2,4-triazole-1-propanenitrile
C6.   alpha-n-butyl-alpha-(2-methylphenyl)-1H-1,2,4-triazole-1-propanenitrile
C7.   alpha-n-butyl-alpha-(2-cyanophenyl)-1H-1,2,4-triazole-1propanenitrile
C8.   alpha-n-butyl-alpha-(3-methoxyphenyl)-1H-1,2,4-triazole-1-propanenitrile
C9.   alpha-n-butyl-alpha-(4-methoxyphenyl)-1H-1,2,4-triazole-1-propanenitrile
C10  alpha-(4-methoxyphenyl)-alpha-n-propyl-1H-1,2,4-triazole-1-propanenitrile
C11.  alpha-n-butyl-alpha-(4-ethoxyphenyl)-1H-1,2,4-triazole-1-propanenitrile
C12.   alpha-n-butyl-alpha-(2,4-dichlorophenyl)-1H-1,2,4-triazole-1-propanenitrile The structure of Samples 1-32 and Comparative Samples C1-C12 are set forth in Table 1 below.

TABLE 1

| Sample | $X_n$ | R' |
|---|---|---|
| 1 | 2 OMe | Methyl |
| 2 | 2 OMe | n-propyl |
| 3 | 2 OMe | n-butyl |
| 4 | 2 OMe | iso-butyl |
| 5 | 2 OMe | n-pentyl |
| 6 | 2 OMe | iso-pentyl |
| 7 | 2 OMe | n-hexyl |
| 8 | 2 OEt | n-propyl |
| 9 | 2 OEt | n-butyl |
| 10 | 2 OEt | iso-butyl |
| 11 | 2 OEt | n-pentyl |
| 12 | 2 OEt | iso-pentyl |
| 13 | 2 OPr | n-propyl |
| 14 | 2 OPr | n-butyl |
| 15 | 2 OPr | iso-butyl |
| 16 | 2 OPr | n-pentyl |
| 17 | 2 OBu | n-butyl |
| 18 | 2 OPentyl | n-butyl |
| 19 | 2 OMe, 4 Cl | n-butyl |
| 20 | 2 O(iso-Pr) | n-butyl |
| 21 | 2 OAllyl | n-butyl |
| 22 | 2 OMe, 5 Cl | n-butyl |
| 23 | 2 OMe, 5 Cl | n-propyl |
| 24 | 2 OEt, 5 Cl | n-butyl |
| 25 | 2 OEt, 5 Cl | n-propyl |
| 26 | 2 OMe | $(CH_2)_3CF_3$ |
| 27 | 2 OMe | $(CH_2)_2CH=CH_2$ |
| 28 | 2 OEt | $(CH_2)_3CF_3$ |
| 29 | 2 OEt | $(CH_2)_2CH=CH_2$ |
| 30 | 2 OMe | $CH_2CH=CH_2$ |
| 31 | 2 OMe | $\underset{CH_2C=CH_2}{\overset{Cl}{\mid}}$ |
| 32 | 2 OMe | $\underset{CH_2CHCH_2}{\overset{CH_2}{\diagup\diagdown}}$ |
| C1 | H | n-butyl |
| C2 | H | n-propyl |
| C3 | H | n-pentyl |
| C4 | 2 F | n-butyl |
| C5 | 2 Cl | n-butyl |
| C6 | 2 $CH_3$ | n-butyl |
| C7 | 2 CN | n-butyl |
| C8 | 3 OMe | n-butyl |
| C9 | 4 OMe | n-butyl |
| C10 | 4 OMe | n-propyl |
| C11 | 4 OEt | n-butyl |
| C12 | 2,4 Cl | n-butyl |

Other examples which are included in the present invention include:

| Sample | $X_n$ | R' |
|---|---|---|
| 33 | 2 OH | n-butyl |

-continued

| Sample | $X_n$ | R' |
|---|---|---|
| 34 | 2 OHexyl | n-propyl |
| 35 | 2 O(3-Butenyl) | iso-butyl |
| 36 | 2 OMe | n-octyl |
| 37 | 2 OEt | cyclopentyl |
| 38 | 2 OMe | cyclohexyl |
| 39 | 2 OMe | cyclobutylmethyl |
| 40 | 2 OEt | cyclopropylethyl |

The compounds of the present invention possess curative, residual and preventive antifungal properties against a broad spectrum of phytopathogenic fungi. They may act as systemic and/or contact fungicides. Examples of such fungi include wheat powdery mildew (*Erysiphe graminis*), rice blast (*Piricularia oryzae*), peanut early leaf spot (*Cercosoora arachidicola*), wheat leaf rust (*Puccinia recondita*), wheat stem rust (*Puccinia graminis*), barley net blotch (*Helminthosporium teres*), cucumber powdery mildew (*Sphaerotheca fuliginea*), rice sheath blight (*Rhizoctonia solani*), cucumber downy mildew (*Pseudoperonospora cubensis*), grape downy mildew (*Plasmopora viticola*), tomato late blight (*Phytophthora infestans*) and Helminthosporium leaf spot (*Cochliobolus miyabeanus*).

The compounds of the present invention show unexpected and superior activity against rice diseases, particularly rice blast. The compounds show superior protective, curative and residual activity against rice blast via foliar application. The compounds also show good systemic activity, both protective and curative. While the residual systemic activity and initial activity on rice sheath blight via foliar application is surpassed by some of the comparative samples, the compounds of the present invention do show good residual activity on blast via water surface treatment and rice sheath blight.

Due to the combination of superior activity on rice blast via foliar application and good systemic activity on rice blast via water surface treatment, the compounds of the present invention are more versatile. For that reason the compounds are considered to be superior to the comparative samples.

The triazoles of the present invention can be prepared by conventional synthesis routes. For example, the triazoles may be prepared by nucleophilic displacement of the alkylated phenylacetonitrile bromide (V) by a salt, preferably an alkali metal salt, of the triazole, generally about 1 to about 3 equivalents. This reaction can be run either neat or, preferably, in an appropriate solvent such as dimethylsulfoxide (DMSO), N,N-dimethylformamide (DMF), toluene or xylene at a temperature from about 0° C. to about 150° C., preferably from about 25° to about 100° C. The bromide (V) is prepared by bromomethylation of the alkylated phenylacetonitrile (IV) by methylenebromide (generally about 1.1 to about 2 equivalents) under basic conditions, e.g., sodium or potassium hydroxide, sodium or potassium hydride, potassium methoxide and potassium-t-butoxide (generally about 1.1 to about 2 equivalents) preferably with the use of a solvent such as DMSO with sodium hydroxide or DMF with the hydrides and oxides, at a temperature from about 0° to about 150° C., preferably from about 25° to about 100° C. The alkylated phenylacetonitrile (IV) can be prepared by phase transfer alkylation of the appropriately substituted benzylcyanides (III) with generally about 1 to about 2 equivalents of an alkyl halide R'X' (wherein R' is as defined above and X' is, for example, Cl, Br, I, tosylate or mesylate) in the presence of a strong base, e q., 50% (w/w) sodium hydroxide or another metal alkoxide, and a catalyst, e.q., tetrabutylammonium bromide. Both the benzylcyanides and the alkyl halides can be readily prepared by techniques known from the literature. This synthesis scheme is shown below:

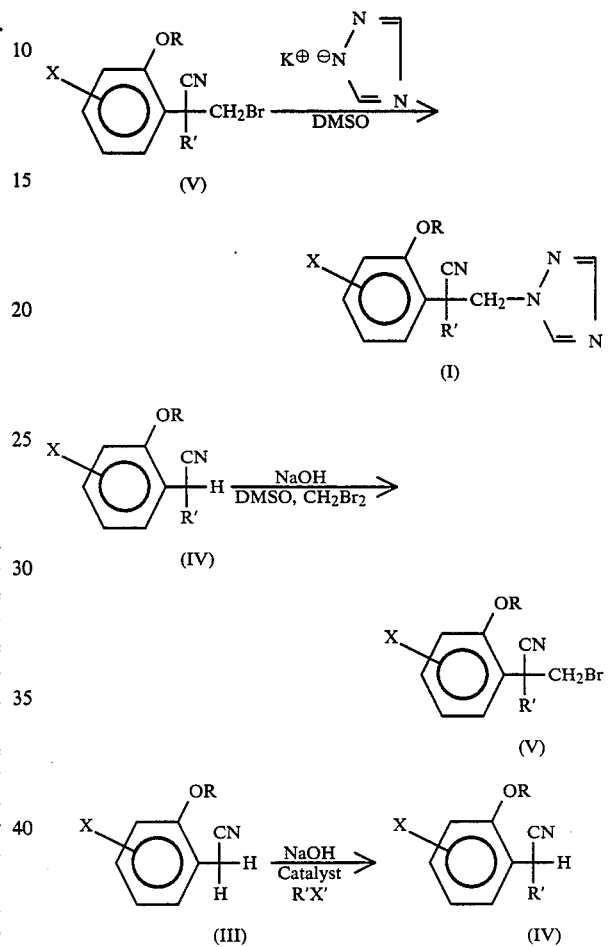

The acid addition salts of the triazoles of this invention can be prepared by standard techniques well-known in the art. For example, the triazole of formula (I) can be dissolved in an appropriate solvent such as diethyl ether, tetrahydrofuran, ethanol, methanol and the like or combinations thereof and treated with an equivalent or excess amount of a mineral or organic acid which may or may not be dissolved in an appropriate solvent, the mixture is then either cooled or evaporated to give the salt which can either be used as such or recrystallized from an appropriate solvent or combination of appropriate solvents.

The metal salt complexes of the above triazoles of this invention can be prepared by adding dropwise, with stirring, a stoichiometric amount of a metal salt dissolved in an appropriate solvent or combination of solvents to a solution of the triazole of formula (I) dissolved in a similarly appropriate solvent or combination of solvents. The reaction mixture is briefly stirred and the solvent is removed under reduced pressure to give the metal salt complex of the respective triazoles of formula (II).

The metal salt complexes can also be prepared by mixing stoichiometric or excess amounts of the metal salt and a triazole of formula (I) in the desired amount of solvent containing the appropriate adjuvants just prior to spraying the plants. Adjuvants that may be included in this "in situ" preparation may be detergents, emulsifiers, wetting agents, spreading agents, dispersing agents, stickers, adhesives, and the like which are used in agricultural applications.

Solvents that can be utilized in these procedures include any polar solvent, e.g., water, methanol, ethanol, isopropanol or ethylene glycol and any aprotic dipolar solvent, e.g., dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Any appropriate anion, e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

The compounds of this invention possess an asymmetric carbon atom and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The enantiomorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a dispersing agent and a finely divided solid, such as clays, inorganic silicates and carbonates, and silicas, and optionally incorporating wetting agents and sticking agents in such mixtures. The concentration of active ingredients in such formulations is usually in the range of from about 20% to about 98%, preferably from about 40% to about 75%. A typical wettable powder is made by blending 50 parts of alpha-n-butyl-alpha-(2-methoxyphenyl)-1H-1,2,4-triazole-1-propanenitrile, 45 parts of a synthetic precipitated hydrated silicon dioxide sold under the trademark Hi-Sil®, 1 part sodium lauryl sulfate and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex® 7.

Dusts are prepared by mixing the triazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application can be readily determined by one in the art depending upon the type of equipment used, the desired method, timing and frequency of applications, plants to be treated and diseases to be controlled. Generally, however, the fungicidal compounds of the present invention will be applied in an amount of from about 0.01 to about 20 pounds of active ingredient per acre when applied foliarly or to the soil.

As a seed protectant, the amount of the compound coated on the seeds is usually from about 0.05 to about 4 ounces of active ingredient per hundred pounds of seed and preferably from 0.1 to about 1 ounce per hundred pounds of seed. As a soil fungicide the compounds can be incorporated in the soil or applied to its surface usually at a rate of from about 0.05 to about 20 pounds, preferably from about 0.02 to about 10 pounds and more preferably from about 0.1 to about 3 pounds of active ingredient per acre. As a foliar fungicide, the compounds are usually applied to growing plants at a rate of from about 0.01 to about 10 pounds, preferably from about 0.02 to about 5 and more preferably from about 0.03 to about 1 pound of active ingredient per acre.

Fungicides which can be combined with the fungicides of this invention include:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structure such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-60(o-chloroanilino)-s-trizaine, diethyl phthalimidophosphorothioate, 4-butyl-1,2,4-triazole, 5-amino-1[bis(dimethylamino)-phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox) methyl 1-(butylcarbamoyl)-2-benzimidazole carbamate-(benomyl), 2-(4'-thiazolyl)benzimidazole-(thiabendazole), 4-(2-chlorophenyldrazono)-3-methyl-5-isoxazolone, pyridine-2-thio-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin,alpha-(phenyl)-alpha-(2,4-dichlorophenyl)-5-pyrimidinylmethanol (triarimol), cis-N-[(1,1,2,2-tetrachloroethyl)thio]-4-cyclohexene-1,2-dicarboxyimide, 3-[2-(3,5-dimethyl-2-oxycyclohexyl)-2hydroxy]-qlutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisoohthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasucamycin and streptomycin;

(f) copper-based fungicides such as: cuprous oxide, basic cupric chloride, basic copper carbonate, copper naphthenate, and Bordeaux mixture;

(g) other rice fungicides such as: tricylazole, iso-prothiolane, probenazole, propiconazole, edifenphos, O-O-diisopropylbenzyl-thiophosphate, iprodione, procymidone, vinclozolin, benomyl, thiophanate methyl, mepronil, tencycuron and validamycin A; and (h) miscellaneous fungicides such as: diphenyl, dodecylguanidine acetate (dodine), phenylmercuric acetate, N-ethylmercuri-1,2,3,6- tetrahydro-3,6-endomethano-3,4,5,6,7,7-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2bis(3-methoxycarbonyl-2-thioureido)benzene(thiophanatemethyl). The enantiomorphs, acid addition salts and metal salt complexes of this invention can be advantageously employed in various ways. Since these compounds possess broad spectrum fungicidal activity, they can be employed as fungicides in turf, fruit orchards, vegetable crops, cereal crops, golf course applications and the storage of cereal grain. Other applications of this invention will suggest themselves to those skilled in the art of agriculture and horticulture.

EXAMPLES

In summary, the substituted benzylcyanide was synthesized to the alpha-(2-alkoxyphenyl)-alpha-alkyl-1H-1,2,4-triazole-1-propanenitrile in three steps. The benzylcyanide was alkylated in the first step by one of three methods. The alkylated phenylacetonitrile was bromomethylated in the second step by one of four methods. The alkylated triazole propanenitrile was synthesized from the alkylated phenylacetonitrile bromide by nucleophilic displacement with potassium triazole in the third step. In the third step the potassium triazole was either previously prepared and added to the bromide or equal parts of potassium hydroxide, triazole and DMSO was added to an equivalent amount of toluene, heated to 100°–120° C. for 2 hours to distill off the toluene and drive off the azeotropic water and the bromide added to the freshly prepared potassium triazole. In a third method the potassium triazole was prepared in situ by the reaction of potassium carbonate and triazole in a methyl ethyl ketone (MEK) or DMSO solvent. A summary of the three steps and the process of preparation of the Samples 1-32 are set forth in Tables 2 and 3.

TABLE 2

| | STEP 1 | | STEP 2 | | STEP 3 |
|---|---|---|---|---|---|
| 1. | 50% NaOH in DMSO (50% NaOH) | 1. | 50% NaOH in DMSO (50% NaOH) | 1. | KTriazole previously prepared |
| 2. | 50% NaOH with tetrabutyl-ammonium Cl or Br catalyst usually in toluene or DMSO solvent (50% NaOHC) | 2. | 60% NaH in (NaH) | | |
| | | 3. | 60% NaH/35% KH in DMF (NaH/KH) | 2. | KOHTriazole (KOHTriaz) |
| | | 4. | 35% KH in DMF (KH) | 3. | K₂CO₃Triazole (K₂CO₃Triaz) |
| 3. | 60% NaH in DMF (NaH) | | | | |

TABLE 3

| SAMPLE | STEP 1 | STEP 2 | STEP 3 |
|---|---|---|---|
| 1 | 50% NaOHC | 50% NaOH | KOHTriaz |
| 2 | 50% NaOHC | 50% NaOH | KTriazole |
| 3 | 50% NaOHC | 50% NaOH | KOHTriaz |
| 4 | 50% NaOHC | 50% NaOH | KTriazole |
| 5 | 50% NaOHC | 50% NaOH | KTriazole |
| 6 | 50% NaOHC | 50% NaOH | KTriazole |
| 7 | 50% NaOHC | 50% NaOH | KTriazole |
| 8 | 50% NaOH | NaH | KTriazole |
| 9 | NaH | NaH | KTriazole |
| 10 | 50% NaOH | KH | KTriazole |
| 11 | 50% NaOH | NaH/KH | KTriazole |
| 12 | 50% NaOH | NaH | KTriazole |
| 13 | NaH | KH | KTriazole |
| 14 | NaH | NaH/KH | KTriazole |
| 15 | NaH | KH | KTriazole |
| 16 | NaH | KH | KTriazole |
| 17 | NaH | NaH/KH | KTriazole |
| 18 | NaH | KH | KTriazole |
| 19 | 50% NaOHC | 50% NaOH | KTriazole |
| 20 | NaH | KH | KTriazole |
| 21 | NaH | KH | KTriazole |
| 22 | 50% NaOH | 50% NaOH | K₂CO₃Triaz |
| 23 | 50% NaOH | 50% NaOH | K₂CO₃Triaz |
| 24 | 50% NaOH | 50% NaOH | K₂CO₃Triaz |
| 25 | 50% NaOH | 50% NaOH | K₂CO₃Triaz |
| 26 | 50% NaOH | 50% KH | KTriazole |
| 27 | 50% NaOH | 50% KH | KTriazole |

TABLE 3-continued

| SAMPLE | STEP 1 | STEP 2 | STEP 3 |
|---|---|---|---|
| 28 | 50% NaOH | 50% KH | KTriazole |
| 29 | 50% NaOH | 50% KH | KTriazole |
| 30 | 50% NaOH | 50% NaOH | KTriazole |
| 31 | 50% NaOH | 50% NaOH | KTriazole |
| 32 | 50% NaOH | 50% NaOH | KTriazole |

Example 1 sets forth the preparation of a typical compound of the present invention, Sample 11. Following Example 1, examples and discussion of the other process steps listed in Table 2 are presented.

The elemental analysis and melting points for Samples 1–20, 22–25, 30 and 31 are then set forth in Table 4. The amount of oxygen was not measured in all of the samples. The NMR for Samples 21, 26 to 29 and 32 follow Table 4.

TABLE 4

| | Elemental Analysis[1]/Melting Point[2] | | | | | |
|---|---|---|---|---|---|---|
| Sample | Carbon | Hydrogen | Nitrogen | Oxygen | Chlorine | M.P. (°C.) |
| 1 | 64.42 (64.92) | 5.83 (5.93) | 23.14 (20.85) | 6.61 (8.52) | | Oil |
| 2 | 66.62 (65.98) | 6.73 (6.71) | 20.73 (20.37) | 5.92 (7.05) | | 115–116 |
| 3 | 67.58 (67.47) | 7.09 (7.13) | 19.70 (19.37) | | | 94–97 |
| 4 | 67.56 (67.52) | 7.09 (7.11) | 19.71 (19.08) | 5.62 (6.66) | | 97–99 |
| 5 | 68.41 (68.16) | 7.44 (7.47) | 18.79 (18.54) | 5.37 (6.32) | | 70–72 |
| 6 | 68.41 (68.92) | 7.44 (7.44) | 18.79 (18.49) | 5.37 (6.11) | | 116–117 |
| 7 | 69.20 (67.74) | 7.68 (7.42) | 17.93 (15.97) | 5.12 (7.31) | | Oil |
| 8 | 67.58 (68.51) | 7.09 (7.09) | 19.70 (18.41) | 5.63 (6.19) | | 101–104 |
| 9 | 68.43 (69.23) | 7.43 (7.57) | 18.78 (17.41) | | | 75.5–76 |
| 10 | 68.41 (68.24) | 7.44 (7.44) | 18.79 (18.28) | 5.37 (5.35) | | 115–116 |
| 11 | 69.18 (69.41) | 7.75 (7.64) | 17.95 (17.99) | 5.12 (5.66) | | 79–80 |
| 12 | 69.20 (69.81) | 7.94 (8.20) | 17.93 (17.89) | 5.12 (4.20) | | 95–96.5 |
| 13 | 68.41 (68.42) | 7.43 (7.17) | 18.79 (17.94) | 5.36 (5.40) | | 69–70 |
| 14 | 69.18 (68.41) | 7.74 (7.79) | 17.96 (16.70) | 5.12 (5.94) | | Oil |
| 15 | 69.18 (69.32) | 7.74 (7.61) | 17.94 (17.60) | 5.13 (4.99) | | 98–99 |
| 16 | 70.10 (70.03) | 7.74 (7.89) | 17.27 (16.26) | 4.92 (5.42) | | 55–56 |
| 17 | 69.89 (69.66) | 8.03 (8.21) | 17.17 (16.74) | 4.90 (5.72) | | Oil |
| 18 | 70.53 (71.20) | 8.29 (8.49) | 16.46 (14.28) | 4.20 (5.41) | | Oil |
| 19 | 60.28 (58.26) | 6.01 (6.11) | 17.57 (16.51) | | 11.12 (10.64) | Oil |
| 20 | 69.18 (68.18) | 7.74 (7.68) | 17.90 (17.44) | 5.12 (6.86) | | Oil |
| 21 | — | — | — | — | | Oil |
| 22 | 60.25 (60.01) | 6.01 (5.98) | 17.58 (16.82) | 5.02 (5.95) | 11.12 (11.15) | Oil |
| 23 | 59.09 (59.55) | 5.62 (5.81) | 18.39 (16.88) | 5.25 (5.93) | 11.63 (12.07) | 137–140 |
| 24 | 61.32 (61.65) | 6.36 (6.50) | 16.81 (16.41) | 4.81 (5.77) | 10.65 (10.62) | 135–138 |
| 25 | 60.25 (60.39) | 6.01 (6.17) | 17.58 (17.41) | 5.02 (5.24) | 11.12 (11.04) | 105–108 |
| 26 | — | — | — | — | — | Oil |
| 27 | — | — | — | — | — | Resin |
| 28 | — | — | — | — | — | Resin |
| 29 | — | — | — | — | — | 55–60 |
| 30 | 66.06 (67.12) | 6.13 (6.01) | 19.74 (20.89) | 6.22 (5.97) | | 144–145 |
| 31 | 60.03 (59.48) | 5.10 (4.99) | 18.45 (18.51) | 5.54 (5.29) | 10.18 (11.71) | 132–133 |

TABLE 4-continued

| | Elemental Analysis[1]/Melting Point[2] | | | | | |
|---|---|---|---|---|---|---|
| Sample | Carbon | Hydrogen | Nitrogen | Oxygen | Chlorine | M.P. (°C.) |
| 32 | — | — | — | — | — | 105–108 |

[1]% calculated (% actually found)
[2]in °C.

NMR was measured for Samples 21 and 26 to 32. The results are as follows:

Sample 21: NMR 60 MHz (CDCl$_3$): 1.0–2.2 (m, 9H), 4.8–4.9 (s, 2H), 4.9–5.4 (ABc, 2H), 5.5–6.4 (m, 3H), 7.07.6 (m, 4H) and 8.0 (s, 2H).

Sample 26: NMR: 200 MHz (CDCl$_3$): 1.4–2.8 (m, 6H), 4.0 (s, 3H), 4.8–5.0 (ABg, 2H), 6.9–7.4 (m, 4H), and 7.8 (two singlets, 2H).

Sample 27: NMR: 200 MHz (CDCl$_3$): 1.9–2.3 (m, 3H), 2.5–2.7 (m, 1H), 4.0 (s, 3H), 4.8–5.1 (two overlapping doublets, 4H), 5.6–5.9 (m, 1H), 6.8–7.1 (m, 2H), 7.3–7.5 (m, 2H), 7.8 (s, 1H) and 7.9 (s, 1H).

Sample 28: NMR: 200 MHz (CDCl$_3$): 1.2–2.7 (m, 6H), 1.4–1.5 (t, 3H), 4 0–4.2 (ABc, 2H), 4.7–5.0 (ABq, 2H), 6.8–7.8 (m, 2H), 7.2–7.4 (m, 2H) and 7.8 (s, 1H).

Sample 29: NMR: 200 MHz (CDCl$_3$): 1.5–1.6 (t, 3H), 1.9–2.4 (m, 3H), 2.8–2.9 (m, 1H), 4.2–4.4 (ABg, 2H), 4.75.2 (m, 4H), 5.7–5.9 (m, 1H), 6.8–7.1 (m, 2H), 7.3–7.5 (m, H) and 7.9 (two singlets, 2H).

Sample 32: NMR: 200 MHz (CDCl$_3$): 0.3–0.8 (m, 4H), 1.8–1.9 (dd, 1H), 2.5–2.6 (dd, 1H), 4.0 (s, 3H), 4.9–5.1 (ABc, 2H), 6.9–7.1 (m, 2H), 7.3–7.5 (m, 2H), 7.7 (s, 1H) and 7.9 (s, 1H).

The following are examples of the preparation of typical compounds of the present invention.

Example 1: Preparation of alpha-(2-Ethoxyphenyl)-alpha-n-Pentyl-1H-1,2,4-Triazole-1-Propanenitrile (Sample 11)

A) Preparation of 2-(2-ethoxyphenyl)heptanenitrile

A three neck 300 ml flask fitted with a reflux condenser, thermometer and dropping funnel was charged with 18.52 grams (0.15 moles) of commercially available 2-ethoxy benzylcyanide in 50 ml of dimethyl sulfoxide (DMSO). To the reaction was added 17.6 grams (0.165 moles, 1.1 ec.) of 1-chloropentane. While stirring at room temperature, 13.2 grams (0.165 moles) of 50% NaOH in 20 ml of DMSO was added over 20 minutes. A slight exotherm occurred and the reaction mixture was stirred at room temperature for 2 hours after which gas-liquid chromatoqraphy (GLC) indicated the reaction was 92% complete. The reaction was stirred for an additional 3 hours, then water was added followed by 200 ml of ether. After washing with acid and brine, the solvent was concentrated and gave an oil which was distilled under vacuum (160°–165° C. at 0.5 mm) and gave 15.82 grams (47.7% yield) of product.

NMR: 60 MHz (d-CHCl$_3$): 0.9–2.0 (m, 14H), 3.9–4.2 (ABq, 2H), 4.1–4.2 (m, 1H) and 6.7–7.5 (m, 4H).

B) Preparation of 1-bromo-2-cyano-2-(2-ethoxyphenyl)heptane

A 200 ml three-neck flask fitted with a reflux condenser, nitrogen inlet, thermometer and addition funnel was charged with 1.8 grams (0.045 moles, 1.28 ec.) of 60% NaH, washed 2×40 ml of hexane, in 30 ml of dimethyl formamide (DMF). While stirring at room temperature, 1.41 grams of 35% KH (with removal of the mineral oil before washing with hexane, assumed 100% KH, 0.035 moles, 1.0 ec.) in 20 ml of DMF was added. To the reaction was added 8.10 grams (0.0350 moles, 1.0 ec.) of 2-(2-ethoxyphenyl)heptanenitrile in 25 ml of DMF. After stirring at room temperature for 1 hour, 9.15 grams (0.0525 moles, 1.5 eg.) of $CH_2Br_2$ in 25 ml of DMF was added dropwise over 10 minutes. The reaction exothermed slightly and was stirred at room temperature overnight after which GLC indicated the reaction was 80% product. An additional 0.7 g of 100% KH (0.5 ec.) was added in 20 ml of DMF, after washing with 20 ml of hexane, and this was followed by an additional 3.0 grams of $CH_2Br_2$ The reaction was stirred for an additional 3 hours and was complete by GLC. Workup with ether and water gave after concentration 10.97 grams of a thick oil (97.2% yield) which was used directly in the coupling procedure.

(C) Preparation of alpha-(2-ethoxyphenyl)-alpha-n-pentyl-1H-1,2,4-triazole-propanenitrile A single neck 200 ml flask was charged with 10.92 grams (0.0339 moles, 1.0 ec.) 1-bromo-2-cyano-2-(2$ ethoxyphenyl)heptane and 50 ml of DMSO. To the reaction was added 3.99 crams (0.0374 moles, 1.1 ec.) of potassium triazole (KTriazole) in 50 ml of DMSO. The reaction was stirred at room temperature to 130° C. over 2 hours, then kept at 120° C. for 1 hr. The reaction was cooled to room temperature after which GLC indicated 86% product. The reaction was quenched by adding 30 ml of water and 130 ml of ether then washed with brine. Removal of the solvent gave a solid to which ether was added and cooled in a freezer overnite. The product was filtered and gave 4.76 grams (44.9%) of a white solid with a melting point temperature (mpt) of 79°–80° C.

Elemental Analysis calculated for: $C_{18}H_{24}N_4O$ ELEMENTAL _ANALYSIS: Theor. (Found) C, 69.18(69.41); H, 7.75(7.64); N, 17.95(17.99); O, 5.12(5.66).

NMR: 60 MHZ (d-CHCl$_3$): 0.8–2.0 (m, 14H), 4.0–4.5 (ABc, 2H), 4.8–5.2 (ABc) 6.8–7.5 (m, 4H) and 7.9 (br s, 2H).

IR (thin film): 3120(w), 3065(w), 2660(s), 2930(s) 2240(w), 1600(m), 1585(m), 1485(s), 1445(s), 1390(m), 1270(s), 1250(s), 1220(s), 1140(s), 1110(m), 1035(s), 935(m), 960(m), 755(s), 680(s) and 660(m).

Example 2: Alkylation of Benzylcyanide

In a majority of the compounds prepared, alkylation of the substituted benzylcyanide was performed in the presence of NaOH. Samples 8, 10, 11 and 12 were prepared without a catalyst by the procedure set forth in Example 1 A).

Eight of the samples were alkylated in the presence of a catalyst. Usually the catalyst was tetrabutylammonium chloride (TBACl) or bromide (TBABr) in DMSO or toluene solvent. No solvent was required in Samples 3 and 6. DMSO/TBABr was used in Samples 2 and 4. DMSO/TBACl was used in Samples 1, 7 and 19. The solvent used in Sample 5 was toluene.

The temperature employed was usually from 35 to 55° C. after the initial exotherm which was to about 45° C. The reaction was typically stirred for 3 to 18 hours and the product was usually greater than 90% monoalkylated and in most cases was not distilled.

The final procedure for alkylation employed 60% NaH in DMF at room temperature to 50° C. Samples using this procedure were 13, 14, 15, 16, 17, 18, 20 and 21.

The halide used in the alkylation may be either the chloride or the bromide. The reaction was faster with the bromide and there was acceptable dialkylation with the NaOH method. The reaction was slower with alkyl chlorides and again with NaOH greater than 90% monoalkylated was observed. With NaH there was also only a small amount of dialkylation with the chlorides. The bromides were used only with NaOH and the chloroalkyls were used with NaOH and NaH.

10 The catalyst was used in 1–5% molar eguivalents. One to three equivalents of NaOH, usually 2–3 eq., and 1–2 eq. of the alkyl halide were used. With NaH, usually 1.1 to 1.5 eq. of base and 1.1 of alkyl halide were used.

Example 3: Bromomethylation of Alkylated Phenylacetonitrile

Four different conditions were employed for the bromomethylation of the alkylated phenylacetonitrile, all using $CH_2Br_2$ for the homologation. Seven samples used 50% NaOH in DMSO. The remaining samples employed hydride bases with $CH_2Br_2$. The bases used were either NaH or KH or mixtures of each. Table 3 indicates which samples used which base, when a mixture was used usually it was 3:1 NaH/KH. Preferably 1.1 to 3.0 eq. of hydride was used, typically 2.0 eq. and 2–3 ec. of $CH_2Br_2$ With NaOH, usually 2–3 eg. of the base was used and 1.5 eq. of $CH_2Br_2$. After exotherm to 45°–55° C., the hydride reaction was kept at 40°–50° C. for 2–4 hrs.

With NaOH, the reaction proceeded slowly when conventional concentrations were used. Surprisingly, when the concentration of the alkylated phenyl acetonitrile was kept below 20% and the NaOH was added slowly, the reaction would go to completion. Although diluting the reactants was contrary to accepted practices, the reaction proceeded well at 50°–55° C. over 2–6 hrs.

Example 4: Preparation of 1-Bromo-2-cyano-2-(2-methoxyphenyl)hexane Using 50% NaOH/DMSO A 5 liter three neck round bottom flask equipped with mechanical stirrer was charged with 500 grams (2.46 moles, 1.0 ec.) of alpha-n-butyl-alpha-(2-methoxyphenyl) hexanenitrile and 2500 ml of DMSO and 513 grams of $CH_2Br_2$ (2.95 moles, 1.20 ec.). To the reaction was added dropwise over 3 hours 394 grams (4.92 moles, 2.0 eq.) of 50% NaOH. Upon addition of the base the reaction exothermed to 55° C. and was maintained at that temperature during the addition and for two hours following the completion of the addition. The reaction was 90% complete and was quenched by the addition of water. The product was isolated with ether and washed with water and brine. Distillation of the crude material gave 478 grams of product (66% yield, 90% pure) as a colorless liquid.

NMR: 60 MHz (CDCl$_3$): 0.9–2.6 (m, 9H), 4.0 (s, 3H), 3.1–3.5 (ABc, 2H), and 7.0–7.9 (m, 4H).

Example 5: Preparation of 2-Alkoxy Benzylcyanides

The 2-methoxy and 2-ethoxy benzylcyanides which were used as starting materials are commercially available and were usually employed. However, they can be prepared using either procedure described below.

The 2-butoxy; 2-pentoxy; 2-isopropxy; 2-allyloxy and 2-propoxy benzylcyanides were prepared from 2-hydroxy benzylcyanide. The 2-proproxy benzylcyanide was also prepared in an alternative general three step procedure starting from 2-hydroxybenzyl alcohol. The alternative general three step procedure locks one into preparing only one ether at a time since the ether alcohol is synthesized first, then the alcohol is converted to the cyanide.

A) Preparation of 2-hydroxy benzylcyanide and alkylation to 2-pentoxy benzylcyanide

Step 1: Acetylation of 2-hydroxy benzylcyanide Preparation of 2-acetoxybenzylacetate.

A 1 liter round bottom flask was charged with 1.40 moles (173.8 grams) of 2-hydroxybenzyl alcohol and 2.64 moles (2.6 ec.) of acetic anhydride followed by 0.31 eq. (0.43 moles) of pyridine. Upon addition of the pyridine dropwise, the reaction exothermed to 60° C. and was cooled to 50° C. with a water bath during the completion of the addition. The reaction was stirred at room temperature and after 2 hours was complete. The solvent was removed at the rotovap, dissolved in ether, and washed with 1 liter of 10% HCl, 2 x 700 ml of water and 700 ml of brine. The ether was dried over sulfate, filtered, concentrated and cave 280 c (96%) of product.

NMR: 90 MHz (CDCl$_3$): 1.73 (s, 3H), 1.98 (s, 3H), 5.10 (s, 2H) and 7.1–7.5 (m, 4H).

Step 2: Reaction of 2-acetoxybenzylacetate with NaCN/DMF- Preparation of 2-hydroxy benzylcyanide A 2 liter 4-neck round bottom flask was charged with 93.6 grams (0.45 moles) of 2-acetoxybenzylacetate in 900 ml of DMF and 48.1 cms (0.98 moles, 2.18 ec.) of NaCN was added. Upon addition the reaction exothermed slowly to 60° C. and then was stirred for 18 hours at room temperature. The reaction mixture was then poured into 7 liters of water, acidified with H2S04 and extracted with 3×500 ml of ether. The combined ether extraction was washed with 2×1 liter of H20 and dried over sulfate. The solvent was filtered, concentrated and 53 grams of a beige solid resulted. The solid was dissolved in 150 ml of hot toluene, cooled to 0° C. and kept ovenight. The solid which resulted was filtered and dried and gave 37 gms (61.8%) of a light orange solid mpt. 117°–119° C.

NMR: 60 MHZ (CDCl$_3$): 3.8 (s, 2H), 6.8–7.4 (m, 4H) and 9.1–9.3 (br s, 1H).

IR (nujol) cm: 3300–3400 (br), 2265 (s), 1600 (s), 1460 (s), 1370 (s), 1275 (s), 1235 (s), 1175 (m), 1100 (m) 1040 (w), 940 (w), 840 (w), 820 (w), 770 (s) and 730 (m).

Step 3: Alkylation of 2-hydroxy benzylcyanide—Preparation of 2-pentoxy benzylcyanide A single neck 200 ml round bottom flask equipped with a reflux condenser and N2 inlet was charged with 13.3 grams of 2-hydroxy benzylcyanide (0.10 mole, 1.0 eq.) and 21.7 gms of anhydrous K$_2$CO$_3$ (0.15 mole, 1.5 eq.). To this was added 50 ml of CH$_3$CN and followed by 23.6 g of n-pentyl iodide (0.12 mole, 1.2 ec.). The reaction was stirred at 50° C. for 1 hour, then at room temperature for 4 hours after which gas-liquid chromatography (GLC) indicated the reaction mixture was 76% product. The reaction was stirred at room temperature overnight and was 92% product as indicated by GLC. Fifty ml of water was added followed by addition to 200 ml of ether which was acidifed with 30 ml of 10% HCl. After washing with water, drying and concentrating, the crude product was distilled to give 11.83 grams (58.3% yield).

NMR: 90 MHz (CDCl$_3$): 0.9–2.0 (m, 9H), 3.6 (br s, 2H), 3.9–4.1 (t, 2H), 6.8–7.0 (t, 2H) and 7.1–7.3 (t, 2H).

B) Preparation of 2-propoxy benzylcyanide via a general three step procedure

Step 1: Preparation

A 2 liter flask was charged with 271 g (2.18 moles, 1.0 eq.) of 2-hydroxybenzyl alcohol and 301 grams (2.18 moles, 1.0 eq.) of anhydrous K$_2$CO$_3$ in 700 ml of methyl ethyl ketone (MEK). The mixture was stirred at reflux for 30 minutes after which 390 grams (2.29 moles, 1.05 eq.) of n-propyl iodide was added. The mixture was stirred at reflux for 12 hours then cooled to room temperature, diluted with water, and neutralized with acid. After extracting with ether, drying and concentrating, the reaction gave 358 grams of a light yellow oil product (98% yield).

NMR: 60 MHz (CDCl$_3$): 0.9–1.3 (t, 3H), 1.6–2.3 (hextet, 2H) 2.8–3.0 (br s, 1H), 3.9–4.2 (t, 2H), 4.7–4.9 (br s, 2H) and 6.8-7.3 (m, 4H).

Step 2: Preparation of 2-propoxybenzyl chloride

A 2 liter flask was charged with 316 grams (1.9 moles, 1.0 eg.) of 2-propoxybenzyl alcohol and 15 grams of pyridine (0.0126 moles) in 750 ml of toluene. 237 grams (1.99 moles, 1.01 ec.) of thionyl chloride was slowly added dropwise, allowing the reaction mixture to reflux during the addition. The reaction was stirred 4 hours at room temperature after which the toluene and thionyl chloride were removed under reduced pressure. To the remaining oil was added water and ether and washed with saturated NaHCO3 Drying and removal of the solvent gave 367 grams (100% yield) of a red oil.

NMR: 60 MHz (CDCl$_3$): 1.0–1.4 (t, 3H), 1.7–2.3 (hextet, 2H) 4.0–4.3 (t, 2H), 4.9 (s, 2H) and 6.9–7.7 (m, 4H).

Step 3: Preparation of 2-propoxy benzylcyanide

Note: To obtain the best results in this reaction, distilled chloride should be used.

A 2 liter flask was charged with 367 grams (1.90 moles, 1.0 ec.) of crude 2-propoxybenzyl chloride in 700 ml of DMSO. The reaction is cooled by a water bath and 102 grams of sodium cyanide (2.09 moles, 1.1 eq.) was added and allowed to warm to 50° C. After the exotherm was complete, the reaction was stirred at room temperature overnight then worked up with water, dilute acid and ether. Removal of the solvent was followed by distillation (120°–150° C. at 1 mm) and gave 180 grams (54% Yield) of a light yellow oil.

NMR: 60 MHz: 1.0–1.4 (t, H), 1.7–2.2 (hextet, 2H), 3.8 (s, 2H), 4.05–4.3 (t, 2H) and 7.1–7.7 (m, 4H).

Example 6: Preparation of alpha-n-Butyl-alpha-(5-Chloro-2-Ethoxyphenyl)-1H-1,2,4-Triazole-1

Propanenitrile (Sample 24)

A three-neck 300 ml round bottom flask equipped with a stirrer, thermometer and condenser was charged with 18.1 grams (0.13 moles) of anhydrous K2C03, 9.1 grams (0.13 moles) of 1,2,4-triazole in 80 ml of DMSO. The mixture was heated to 150° C. and maintained at that temperature for one hour. The reaction was cooled to 120° C. and 22.5 grams (0.065 moles) of 1-bromo-2-cyano-2-(5-chloro-2ethoxyphenyl) hexane was added dropwise and the reaction warmed to 125° C. The reaction was stirred for 2.5 hours after which gas-liquid chromotography showed the reaction was complete.

The reaction mixture was poured into 500 ml of water and extracted twice with 200 ml of ethyl acetate. After washing the mixture twice with 200 ml of water and 200 ml of saturated sodium chloride, the solution was dried and filtered. The solvent was removed on a rotovap after which the product solidified and was titrated with hexane and stirred over night. The product was filtered and dried to give 17.7 grams of a white solid having a melting point yield of 135°–138° C. (81.5% yield).

Elemental Analysis calculated for: $C_{17}H_{21}ClN_4O$
ELEMENTAL ANALYSIS: Theor. (Found) C, 61.32 (61.65); H, 6.36 (6.50); N, 16.81 (16.41); O, 4.81 (5.77); Cl 10.65 (10.62).

The compounds of the present invention were tested for activity against a number of diseases. The test compounds were dissolved in acetone, methanol and water to form a series of dilutions from 300 ppm to 5 ppm. Depending on when the tests were run, various serial dilutions were used, e.g., 300, 75, 19, 5 or 100, 25, 6. Unless otherwise indicated the plants were sprayed to runoff with a mechanical sprayer the same day or the day before innoculation. The protocol for Wheat Powdery Mildew (WPM) and Rice Blast (RB) were as follows:

WHEAT POWDERY MILDEW (WPM)-Erysiphe graminis

Wheat seedlings cultivar VICTORY 283 were grown in redi-earth. The seedlings were six to seven days old and were fertilized with LIQUID-M fertilizer before use to promote vigorous growth throughout the test period.

The seedlings were inoculated by shaking sporulating culture plants over them, disseminating mildew spores. The inoculated seedlings were placed in subirrigation trays in a controlled temperature room which provided a 70° F. environment for disease development.

Since WPM development is greatly affected by volatile chemicals, the pots were spread out as much as possible and the trays are separated according to dose by plastic sheets. Disease development was rated seven to ten days after inoculation on a percent control basis.

RICE BLAST (RB)-Pricularia oryzae

Seedlings of the rice cultivar M-201 were grown in a greenhouse at 20°–30° C. in 2-inch pots containing unsterilized soil and Turf-Builder* soil/fertilizer for 14 days. The rice plants were not trimmed before use.
* Turf-Builder is a trademark of Scotts Company.

Inoculum was produced in-vitro on oatmeal agar (50g Gerber** baby oatmeal, 20g bacto agar, 10g bacto dextrose, 100ml deionized water). The plates were inoculated with a mycelial plug (7-14 days old) of Piricularia oryzae. The outer edge of the dark region was used in the transfer. Inoculated plates were maintained at room temperature under constant fluorescent light.
** Gerber is a trademark of Gerber Products Co.

P. oryzae plates 10–14 days old were flooded with a solution containing 0.25g sodium oleate, 2g gelatin and 1000ml deionized water. The plates were scraped with a rubber policeman to release conidia, filtered through a double layer of cheesecloth and spore suspension adjusted to 25000-30000 spores/ml using a hemacytometer.

The spore suspension was sprayed on opposite sides of a double row of rice plants using a hand sprayer. Sufficient inoculum was applied to achieve uniform distribution from soil to tip of rice leaves on opposite sides of each pot (approx. 50ml/50 pots). The hand sprayer was shook after each pass to keep the solution in suspension.

The inoculated plants were immediately placed in a humidity cabinet at 25° C. for 66 hours prior to moving them to the greenhouse under a plastic tent. The plants were subirrigated but not allowed to stand in water more than 2 hours. The plastic sides of the tent were lifted during work hours and closed at end of day.

After 76 hours under greenhouse conditions the bioassay plants were observed and the percent disease control (as compared to inoculated control) was estimated.

The compounds were tested at different dose rates depending on when the tests were run. The results of the tests are set forth in Table 5 for one dose rate for each compound. If the compound was tested more than once at the dose rate, the average is reported.

TABLE 5

| PPM Dilution Sample | Fungicidal Activity (% control) | | | | | |
|---|---|---|---|---|---|---|
| | WPM | | | RB | | |
| | 300 | 200 | 100 | 300 | 200 | 100 |
| 1 | 78 | | | 45 | | |
| 2 | 100 | | | 70 | | |
| 3 | 100 | | | 95 | | |
| 4 | 100 | | | 100 | | |
| 5 | 100 | | | 70 | | |
| 6 | 100 | | | 84 | | |
| 7 | | 100 | | | | 0 |
| 9 | 100 | | | 100 | | |
| 10 | | | 100 | | | 0 |
| 11 | | | 100 | | | 0 |
| 12 | | 100 | | | 0 | |
| 13 | | | 99.5 | | | 75 |
| 14 | | | 100 | | | 96 |
| 15 | | | 99 | | | 94 |
| 16 | | | 95 | | | 95 |
| 17 | | | 99 | | | 87.5 |
| 18 | | | 99 | | | 50 |
| 19 | | 100 | | 90 | | |
| 20 | | | 100 | | | 90 |
| 21 | | | 95 | | | 80 |
| 22 | | | 100 | | | 100 |
| 23 | | | 100 | | | 95 |
| 24 | | | 100 | | | 85 |
| 25 | | | 100 | | | 99.5 |
| 26 | | | 99 | | | 90* |
| 27 | | | 99 | | | 80 |
| 28 | | | 100 | | | 80 |
| 29 | | | 90 | | | 80 |
| 30 | | 100 | | | 80 | |
| 31 | | 100 | | | 80 | |
| 32 | | | 100 | | 80 | |

*At 25 PPM.

EXAMPLE 7: In-Vitro Activity Against Piricularia Oryzae

Compounds of the present invention and comparative samples were tested for in-vitro activity against Piricularia oryzae by poisoned agar test.

The poison agar tests used to find EC75 values were done as follows: the compounds were dissolved in methanol and serially diluted in hot, autoclaved potato dextrose agar so that 0.1, 1, 10 or 100 ppm solutions resulted. After the agar solidified in petri dishes hyphal plugs or mycelial disks of Piricularia oyrzae were placed on the agar and incubated at room temperature for 6 or 7 days. Measurements of colony diameter were converted into EC75 through probit analysis. The results are shown in Table 6.

TABLE 6

In-vitro Activity Against Piricularia Oryzae - EC$_{75}$ (in ppm)

| Compound | Test 1 | Test 2 | Test 3 |
|---|---|---|---|
| 2 | | A | |
| 3 | A | B | B |
| 4 | | A | |
| 5 | | A | |
| 6 | | C | |
| 7 | | A | |
| 8 | | A | |
| 9 | | A | B |
| 11 | | A | |
| 14 | | A | |
| 17 | | A | |
| 19 | | A | B |
| C1 | C | C | C |
| C2 | | C | |
| C3 | | C | |
| C4 | D | D | E |
| C6 | D | D | D |
| C7 | E | | |
| C8 | | D | |
| C9 | E | E | E |
| C10 | | E | |
| C12 | | | D |

A = ≦0.5
B = >.5 and ≦1.5
C = >1.5 and ≦5.0
D = >5.0 and ≦10.0
E = >10.0

Example 8: Rice Blast Activity

Paddy applied rice blast activity (RBP) was determined on two different occasions. In the first test, two week old Nato rice plants in 3 inch pots were placed in 24 oz. "cottage cheese" containers. The pots were then flooded for the duration of the test with 500 ml of 2.5, 5, 10, 20 or 40 ppm fungicide solutions. One week later, the plants were inoculated with *Piricularia oryzae* (approx. 25,000 spores/ml). Then the plants are incubated for 24 hours in the dark, with mist at 23° C. The plants were then further incubated for 6 days in humidity tents in the greenhouse. The plants were evaluated by counting expanding lesions. There were 3 pots per treatment, each containing about 30 plants.

In the second test, ten-day old rice plants were flooded with 80, 40, 20, 10, 5 and 2.5 ppm fungicide solutions. After one week in the greenhouse, the plants were inoculated with a spore suspension of *Piricularia oryzae* (5×10$^5$ spores/ml) and incubated under mist for 3 days at 21° C. The paddies were subsequently transferred to humidity tents in the greenhouse and disease severity was estimated 4 days later based on the incidence of sporulating lesions relative to untreated controls.

The results of the two tests for the 5 ppm concentration and the EC$_{75}$ are set forth in Table 7.

TABLE 7

| | Paddy Applied Rice Blast | | | |
|---|---|---|---|---|
| | Test 1 | | Test 2 | |
| Compound | % Disease Control at 5 ppm[1] | EC$_{75}$[2] | % Disease Control at 5 ppm[1] | EC$_{75}$[3] |
| 3 | 5 | A' | 1 | A" |
| 9 | 4 | A' | — | — |
| 19 | 9 | B' | — | — |
| C1 | 11 | A' | 3 | C" |
| C4 | 11 | D' | 7 | D" |
| C6 | 10 | B' | — | D" |
| C7 | — | — | — | E" |
| C9 | 11 | E' | 10 | — |
| C10 | — | — | — | E" |
| C12 | 11 | E' | 8 | D" |

[1] = 100% of disease controlled
2 = <100% and ≧90% disease controlled
3 = <90% and ≧80% disease controlled
4 = <80% and ≧70% disease controlled
5 = <70% and ≧60% disease controlled
6 = <60% and ≧50% disease controlled
7 = <50% and ≧40% disease controlled
8 = <40% and ≧30% disease controlled
9 = <30% and ≧20% disease controlled
10 = <20% and ≧10% disease controlled
11 = <10% disease controlled
[2] EC$_{75}$ = concentration in ppm at which 75% of the disease is controlled in comparison to the untreated control plant. A = <10 B = <20 and ≧10 C = <40 and ≧20 D = <80 and ≧40 E = ≧80
[3] A" = <1 B" = <3 and ≧1 C" = <5 and ≧3 D" = <10 and ≧5 E" = <20 and ≧10

The percent of disease control at any specified concentration was considerably higher in Test 2 as compared to Test 1. Further, at higher concentrations in both of the tests, the difference between the samples and comparative samples was less noticeable. This is due to the rapid dropoff in activity of the comparative samples and the rather slow dropoff in activity of the compounds of the present invention.

At the higher concentrations, Comparative Sample C1, the unsubstituted phenyl, compares favorably to the preferred compounds of the present invention. In fact, it performs better than the less preferred Sample 19, the 2-methoxy-4-chloro substituted phenyl. However, if Sample 19 is compared to the corresponding 2,4-dichloro substituted phenyl, Comparative Sample C12, Sample 19 is clearly superior.

The preferred compound, Sample 3, clearly outperformed the comparative samples in Test 2.

Examples 9 and 10: Leaf Blast Control Activity

Leaf blast control activity via foliar application, as well as via paddy or water surface treatment (WST), was tested comparing a number of the compounds of the invention against the unsubstituted phenyl compound, Comparative Sample C1 which is the most active of the comparative samples.

Example 9: Leaf Blast Control Activity Via Water Surface Treatment

Three greenhouse tests on Koshihikari variety of rice were done to test the leaf blast control activity via water surface treatment. Each test was run on four replications with one pot per plot. The plants were sprayed with 2.5 ml/9 cm diameter pot which results in 4 kg ai/Ha using hand spray equipment.

In the first test, the temperature in the greenhouse was maintained between 20° and 35° C. and the temperature in the inoculation room between 25° and 35° C. In the second test, the greenhouse temperature was maintained between 10° and 35° C. and the inoculation room temperature between 15° and 30° C. The temperature during Test 3 was maintained between 23° and 33° C. The humidity was maintained high for each test.

The protective activity was measured under severe, heavy and slight disease pressure. Disease pressure was determined by the percent of infected leaf area of the untreated control. Severe disease pressure indicates greater than 25% of the untreated control was infected; heavy was 12-25%; moderate was 2-12%; and slight was less than 2%.

In Test 1, the disease pressure was severe. Half of the plants were treated 15 days after planting and half were treated 22 days after planting. All the plants were inoculated 29 days after planting and evaluated 36 days after planting.

The disease pressure in Test 2 was rated as heavy. One-half of the plants were treated 17 days after planting and the other half were treated 24 days after planting. All the plants were inoculated 31 days after planting and evaluated 37 days after planting.

In Test 3, the disease pressure was slight. Half of the plants were treated 11 days after planting and the other half 18 days after planting. The plants were inoculated 25 days after planting and evaluated 37 days after planting.

The rice seedlings tested in Test 1 were already slightly infected by rice blast when the artificial inoculation was made. The symptoms by natural infection developed quickly in the inoculation room. Curative activity was determined by evaluating the plants 31 days after planting. This was two days after inoculation and before the effects of the artificial inoculation were visually apparent. The disease pressure for the curative activity was moderate.

The results are set forth in Table 8A.

most preferred compounds when applied by water surface treatment of the paddy water.

Example 10: Leaf Blast Control Activity Via Foliar Application

The protective activity, curative activity and residual activity of Comparative Sample C1 were compared to the activity of a number of the compounds of the present invention.

Four tests on Koshihikari variety of rice in which four replications with one pot per plot were tested. A glass atomizer was used to spray the plants to run-off.

Tests A, B and D were done in a greenhouse while Test C was conducted outdoors. The temperature in the greenhouse was maintained between about 25° and 35° C and the humidity was high for all of the tests.

The disease pressure in Test A wasoderate. The plants were treated 14 days after planting, inoculated 15 days after plantinc and evaluated 25 days after planting.

The disease pressure during Test B was severe. The plants were treated 18 days after planting, inoculated 19 days after planting and evaluated 32 days after planting.

The plants of Test C were subjected to a heavy disease pressure. The plants were treated 28 days after planting, inoculated 30 days after planting and evaluated 37 days after planting.

The curative activity via foliar application was determined in Test D. The disease pressure was severe. The

TABLE 8A

| | | Leaf Blast Control Activity via WST (4 kg ai/Ha) | | | | | | | |
|---|---|---|---|---|---|---|---|---|---|
| | | Protective Activity | | | | | | Curative Activity | |
| Compound | Inoculation Disease Pressure | Test 1 Severe | Test 2 2 WAT Heavy | Test 3 Slight | Test 1 Severe | Test 2 1 WAT Heavy | Test 3 Slight | Test 1 2 WAT Moderate | Test 1 1 WAT Moderate |
| 2 | | 1 | 1 | 1 | 1 | 1 | 4 | 1 | 4 |
| 3 | — | 2 | 3 | 1 | 2 | 4 | 4 | 1 | 4 |
| 4 | | 2 | — | — | 5 | 4 | — | 2 | 6 |
| 5 | | 4 | — | — | 7 | — | — | 4 | 8 |
| 6 | | 3 | 5 | 2 | 3 | 5 | 4 | — | — |
| 8 | | 3 | 3 | 5 | 5 | 4 | 6 | 3 | 6 |
| 9 | | 4 | 6 | 5 | 7 | 7 | 5 | 4 | 7 |
| 12 | | 7 | 6 | — | 9 | 9 | — | 5 | 9 |
| C1 | | 2 | 4 | 3 | 5 | 3 | 4 | 3 | 7 |

WAT = weeks after treatment
1 = ≧99% disease control
2 = ≧96% and <99%
3 = ≧90% and <96%
4 = ≧75% and <90%
5 = ≧60% and <75%
6 = ≧45% and <60%
7 = ≧30% and <45%
8 = ≧15% and <30%
9 = <15%

The test results confirm the previous paddy applied rice blast tests in that the most active comparative sample, while better than some of the less preferred compounds of the present invention, is less active than the plants were inoculated 9 days after planting, treated 10 days after planting and evaluated 20 days after planting.

The results are shown in Table 8B.

TABLE 8B

| | | Leaf Blast Control Activity via Foliar (75 ppm) | | | | | | |
|---|---|---|---|---|---|---|---|---|
| | | Protective Activity | | | Curative Activity | Residual Activity | | |
| Compound | Inoculation Disease Pressure | Test A 1 DAT Moder. | Test B 1 DAT Severe | Test C 2 DAT Heavy | Test D 1 DBT Severe | Test B 7 DAT Severe | Test C 8 DAT Heavy | Test C 15 DAT Moder. |
| 2 | | 1 | 1 | 4 | 2 | 1 | 5 | 6 |
| 3 | | 1 | 1 | 2 | 1 | 2 | 4 | 5 |
| 4 | | 4 | 1 | — | 4 | 2 | — | — |
| 5 | | 2 | 1 | — | 2 | 2 | — | — |
| 6 | | — | — | 3 | — | — | 4 | 8 |
| 8 | | 3 | 1 | 3 | 2 | 2 | 6 | 9 |
| 9 | | 2 | 1 | 3 | 2 | 1 | 6 | 8 |
| 12 | | 3 | 2 | 3 | 2 | 2 | 5 | 4 |

TABLE 8B-continued

| | | Leaf Blast Control Activity via Foliar (75 ppm) | | | | | | |
|---|---|---|---|---|---|---|---|---|
| | | Protective Activity | | | Curative Activity | Residual Activity | | |
| Compound | Inoculation Disease Pressure | Test A 1 DAT Moder. | Test B 1 DAT Severe | Test C 2 DAT Heavy | Test D 1 DBT Severe | Test B 7 DAT Severe | Test C 8 DAT Heavy | Test C 15 DAT Moder. |
| C1 | | 2 | 2 | 5 | 2 | 3 | 8 | 9 |

DAT = days after treatment
DBT = days before treatment
1-9 = see Table 7A

In two of the three tests for protective activity, the compounds of the present invention are clearly superior to Comparative Sample C1 which was the most active of the comparative samples. In the third test, the preferred compounds were equal to or better than the Comparative Sample C1.

With the exception of Sample 4, the compounds of the present invention had a curative activity via foliar application which were superior or equal to Comparative Sample 1. The residual activity via foliar application of the compounds of the present invention are clearly superior to the residual activity of Comparative Sample C1.

As the chain length of the 2-alkoxy substituent lengthens from methoxy to ethoxy to propoxy, the rice blast activity via foliar application generally increases. However, the activity peaks at the chain length of the propoxy and decreases as the chain length is lengthened further in the butoxy and pentoxy substituted compounds.

As the alkoxy chain length increases from the methoxy to the ethoxy to the propoxy, the rice blast activity via water surface treatment generally decreases. Therefore, while the ethoxy and propoxy substituted compounds are preferred for foliar application, the methoxy and ethoxy compounds are preferred for their balanced activity via both foliar and water surface treatment.

What is claimed is:

1. A compound of the formula

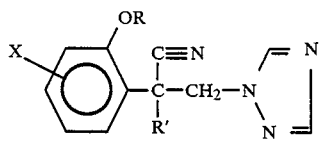

wherein X is a hydrogen, fluorine, chlorine or bromine, R is hydrogen, $(C_1-C_6)$alkyl or $(C_2-C_5)$alkenyl, and R' is unsubstituted or substituted $(C_3-C_8)$alkyl, unsubstituted or substituted $(C_2-C_6)$alkenyl, $(C_3-C_6)$cycloalkyl or $(C_1-C_3)$alkyl$(C_3-C_6)$cycloalkyl wherein the alkyl and alkenyl substituents are one to three halogens and the agronomically acceptable enantiomorphs, acid addition and metal salt complexes thereof.

2. The compound of claim 1 wherein X is hydrogen and R' is $(C_3-C_5)$alkyl and the agronomically acceptable enantiomorphs, acid addition salts and metal salt complexes thereof.

3. The compound of claim 2 wherein R' is n-butyl and the agronomically acceptable enantiomorphs, acid addition salts and metal salt complexes thereof.

4. The compound of claim 1 wherein X is hydrogen and R is $(C_3-C_4)$alkyl and the agronomically acceptable enantiomorphs, acid addition salts and metal salt complexes thereof.

5. The compound of claim 4 wherein R is propyl and R' is $(C_3-C_5)$alkyl and the agronomically acceptable enantiomorphs, acid addition salts and metal salt complexes thereof.

6. The compound of claim 5 named alpha-n-butyl-alpha-(2-propoxyphenyl)-1H-1,2,4-triazole-1-propanenitrile and the agronomically acceptable enantiomorphs, acid addition salts and metal salt complexes thereof.

7. The compound of claim 1 wherein R is methyl and R' is $(C_3-C_5)$alkyl and the agronomically acceptable enantiomorphs, acid addition salts and metal salt complexes thereof.

8. The compound of claim 7 wherein X is hydrogen and the agronomically acceptable enantiomorphs, acid addition salts and metal salt complexes thereof.

9. The compound of claim 8 named alpha-n-butyl-alpha-(2-methoxyphenyl)-1H-1,2,4-triazole-1-propanenitrile and the agronomically acceptable enantiomorphs, acid addition salts and metal salt complexes thereof.

10. The compound of claim 8 named alpha-(2-methoxyphenyl)-alpha-n-propyl-1H-1,2,4-triazole-1-propanenitrile and the agronomically acceptable enantiomorphs, acid addition salts and metal salt complexes thereof.

11. The compound of claim 1 wherein R is ethyl and R' is (C3-C5)alkyl and the agronomically acceptable enantiomorohs, acid addition salts and metal salt complexes thereof.

12. The compound of claim 11 wherein X is hydrogen and the agronomically acceptable enantiomorphs, acid addition salts and metal salt complexes thereof.

13. The compound of claim 12 named alpha-n-butyl-alpha-(2-ethoxyphenyl)-1H-1,2,4-triazole-1-propanenitrile and the agronomically acceptable enantiomorphs, acid addition salts and metal salt complexes thereof.

14. The compound of claim 1 wherein X is fluorine, chlorine or bromine and R' is $(C_2-C_5)$alkyl and the agronomically acceptable enantiomorphs, acid addition and metal salt complexes thereof.

15. The compound of claim 14 named alpha-n-butyl-aloha-(5-chloro-2-methoxyphenyl)-1H-1,2,4-triazole-1-propanenitrile and the agronomically acceptable enantiomorphs, acid addition and metal salt complexes thereof.

16. The compound of claim 14 named alpha-n-butyl-alpha-(5-chloro-2-ethoxyphenyl)-1H-1,2,4 triazole-1propaninitrile and the agronomically acceptable enantiomorphs, acid addition and metal salt complexes thereof.

17. The compound of claim 1 wherein X is hydrogen and R' is halogenated $(C_1-C_4)$alkyl and the agronomically acceptable enantiomorphs, acid addition and metal salt complexes thereof.

18. The compound of claim 1 wherein X is hydrogen and R' is unsubstituted or halogenated $(C_2-C_5)$alkenyl and the agronomically acceptable enantiomorphs, acid addition and metal salt complexes thereof.

19. The compound of claim 1 wherein X is hydrogen and R' is $(C_3-C_6)$cycloalkyl or $(C_1-C_6)$cycloalkyl($C_1-C_3$) alkyl $(C_3-C_6)$cycloalkyl and the agronomically acceptable enantiomorphs, acid addition and metal salt complexes thereof.

20. A fungicidal composition for controlling phytopathogenic fungi which comprises an agronomically acceptable carrier and as the active ingredient a fungicidally effective amount of the compound of claim 1.

21. A fungicidal composition for controlling phytopathogenic fungi which comprises an agronomically acceptable carrier and as the active ingredient a fungicidally effective amount of the compound of claim 9.

22. A fungicidal composition for controlling phytopathogenic fungi which comprises an agronomically acceptable carrier and as the active ingredient a fungicidally effective amount of the compound of claim 10.

23. A fungicidal composition for controlling phytopathogenic fungi which comprises an agronomically acceptable carrier and as the active ingredient a fungicidally effective amount of the compound of claim 13.

24. A fungicidal composition for controlling phytopathogenic fungi which comprises an agronomically acceptable carrier and as the active ingredient a fungicidally effective amount of the compound of claim 15.

25. A fungicidal composition for controlling phytopathogenic fungi which comprises an agronomically acceptable carrier and as the active ingredient a fungicidally effective amount of the compound of claim 16.

26. A method for controlling phytopathogenic fungi which comprises of applying to a plant, to plant seed or to a plant habitat, a fungicidally effective amount of the compound of claim 1.

27. A method for controlling phytopathogenic fungi which comprises of applying to a plant, to plant seed or to a plant habitat, a fungicidally effective amount of the compound of claim 9.

28. A method for controlling phytopathogenic fungi which comprises of applying to a plant, to plant seed or to a plant habitat, a fungicidally effective amount of the compound of claim 10.

29. A method for controlling phytopathogenic fungi which comprises of applying to a plant, to plant seed or to a plant habitat, a fungicidally effective amount of the compound of claim 13.

30. A fungicidal composition for controlling phytopathogenic fungi which comprises an agronomically acceptable carrier and as the active ingredient a fungicidally effective amount of the compound of claim 15.

31. A fungicidal composition for controlling phytopathogenic fungi which comprises an agronomically acceptable carrier and as the active ingredient a fungicidally effective amount of the compound of claim 16.

* * * * *

UNITED STATES PATENT AND TRADEMARK OFFICE
CERTIFICATE OF CORRECTION

PATENT NO. : 4,895,865
DATED : January 23, 1990
INVENTOR(S) : Steven Shaber, Ted Fujimoto It is certified that error appears in the above-identified patent and that said Letters Patent is hereby corrected as shown below:

Column 23, Line 56:

"$(C_1-C_3)$ alkyl (C3-C6) cycloalkyl", change to --$(C_3-C_6)$ cycloalkyl $(C_1-C_3)$ alkyl--.

Column 24, Line 43:

"R' is (C3-C5) alkyl", change to --R' is $(C_3-C_5)$ alkyl--.

Column 24, Line 58:

"aloha", change to --alpha--.

Column 25, Lines 9-10:

"and R' is $(C_3-C_6)$ cycloalkyl or $(C_1-C_6)$ cycloalkyl $(-C_1-C_3)$ alkyl $(C_3-C_6)$ cycloalkyl and the", change to --and R' is $(C_3-C_6)$ cycloalkyl or $(C_3-C_6)$ cycloalkyl $(C_1-C_3)$ alkyl and the--.

Signed and Sealed this

Sixteenth Day of April, 1991

*Attest:*

HARRY F. MANBECK, JR.

*Attesting Officer*   *Commissioner of Patents and Trademarks*